United States Patent
Everett et al.

(10) Patent No.: US 8,050,504 B2
(45) Date of Patent: Nov. 1, 2011

(54) METHOD AND APPARATUS FOR MEASURING MOTION OF A SUBJECT USING A SERIES OF PARTIAL IMAGES FROM AN IMAGING SYSTEM

(75) Inventors: Matthew J. Everett, Livermore, CA (US); Claus Flachenecker, Hayward, CA (US); Martin Hacker, Jena (DE); Scott A. Meyer, Livermore, CA (US); Keith E. O'Hara, San Ramon, CA (US); Rick A. Williams, Orinda, CA (US)

(73) Assignee: Carl Zeis Meditec, Inc., Dublin, CA (US)

( * ) Notice: Subject to any disclaimer, the term of this patent is extended or adjusted under 35 U.S.C. 154(b) by 0 days.

(21) Appl. No.: 12/861,672

(22) Filed: Aug. 23, 2010

(65) Prior Publication Data
US 2011/0043757 A1 Feb. 24, 2011

Related U.S. Application Data (62) Division of application No. 11/389,351, filed on Mar. 24, 2006, now Pat. No. 7,805,009.

(60) Provisional application No. 60/668,785, filed on Apr. 6, 2005.

(51) Int. Cl.
*G06K 9/68* (2006.01)
*G06K 9/00* (2006.01)

(52) U.S. Cl. ....................... 382/218; 382/131

(58) Field of Classification Search ............. 382/151, 382/128, 131–132, 181, 209, 218, 294; 358/208; 351/208, 209
See application file for complete search history.

(56) References Cited

U.S. PATENT DOCUMENTS

| | | | |
|---|---|---|---|
| 4,135,791 A | 1/1979 | Govignon | |
| 4,213,678 A | 7/1980 | Pomerantzeff et al. | |
| 4,732,466 A | 3/1988 | Humphrey | |
| 4,768,873 A | 9/1988 | Webb | |
| 4,856,891 A | 8/1989 | Pflibsen et al. | |
| 5,575,286 A | 11/1996 | Weng et al. | |
| 5,644,642 A | 7/1997 | Kirschbaum | |
| 5,729,008 A | 3/1998 | Blalock et al. | |
| 5,767,941 A | 6/1998 | Ferguson | |
| 5,943,115 A | 8/1999 | Ferguson | |
| 5,975,697 A | 11/1999 | Podoleanu et al. | |
| 6,283,954 B1 | 9/2001 | Yee | |
| 6,295,374 B1 * | 9/2001 | Robinson et al. | 382/218 |
| 6,325,512 B1 | 12/2001 | Wei | |

(Continued)

OTHER PUBLICATIONS

In re U.S. Appl. No. 11/331,567, filed Jan. 13, 2006, Matthew J. Everett by et al., entitled Method of Motion Correction in Optical Coherent Tomography Imaging.

(Continued)

*Primary Examiner* — Daniel Mariam
(74) *Attorney, Agent, or Firm* — Morrison & Foerster LLP (57) ABSTRACT

A line scan imager is used to determine the motion of a subject. Each line of image data from the line scan imager is compared with a reference image. The location of a matching line in the reference image reveals the displacement of the subject. The current subject displacement can be determined based on each line of image data. The resulting displacement information can be used to correctly place other optical beams on the subject. The method can be applied to tracking the human eye to facilitate measurement, imaging, or treatment with a beam of optical radiation.

16 Claims, 3 Drawing Sheets

U.S. PATENT DOCUMENTS

| | | |
|---|---|---|
| 6,501,551 B1 | 12/2002 | Tearney et al. |
| 6,726,325 B2 | 4/2004 | Xie et al. |
| 6,736,508 B2 | 5/2004 | Xie et al. |
| 6,758,564 B2 | 7/2004 | Ferguson |
| 6,769,769 B2 | 8/2004 | Podoleanu et al. |
| 7,118,216 B2 | 10/2006 | Roorda |
| 7,404,640 B2 | 7/2008 | Ferguson et al. |
| 7,480,396 B2 | 1/2009 | Teiwes et al. |
| 2003/0199769 A1 | 10/2003 | Podoleanu et al. |
| 2005/0024586 A1 | 2/2005 | Teiwes et al. |
| 2005/0140984 A1 | 6/2005 | Hitzenberger |

OTHER PUBLICATIONS

D.X. Hammer et al., Image stabilization for scanning laser ophthalmoscopy, *Optics Express*, vol. 10, No. 26, Dec. 30, 2002, 8 pages in length.

D.X. Hammer et al., "Active retinal trackerr for clinocal optical cohernce tomography systems," *Journal of Biomedical Optics*, vol. 10, No. 2, Mar./Apr. 2005, pp. 024038-1-024038-11.

D. Huang, et al., "Optical Coherence Tomography," *Science*, vol. 254, No. 5035, Nov. 22, 1991, pp. 1178-1181.

J.B. Mulligan, Recovery of motion parameters from distortions in scanned images, *Proceedings of the NASA Image Registration Workshop (IRW97)*, Goddard space flight center, Maryland (1997), 15 pages in length.

E. Naess et al., "Computer-assisted laser photocoagulation of the retina-a hybrid tracking approach," *Journal of Biomedical Optics*, vol. 7, No. 2, Apr. 2002, pp. 179-189.

A.Gh. Podoleanu et al., "Combined optical coherence tomograph and scanning laser ophthalmoscope," *Electronics Letters*, vol. 34, No. 11, May 28, 1998, 2 pages in length.

J.A. Rogers et al., "Topography and volume measuremetns of the optic nerve using *en-face* optical coherence tomography," *Optics Express*, vol. 9, No. 10, Nov. 5, 2001, pp. 533-545.

S.B. Stevenson et al., "Correcting for minature eye movements in high resolution scanning laser ophthalmoscopy," *Proceedings of the SPIE*, vol. 5688 (2005), pp. 145-151.

\* cited by examiner

METHOD AND APPARATUS FOR MEASURING MOTION OF A SUBJECT USING A SERIES OF PARTIAL IMAGES FROM AN IMAGING SYSTEM

PRIORITY

This application is a divisional of U.S. patent application Ser. No. 11/389,351, filed Mar. 24, 2006. This application claims the benefit of the filing date under 35 U.S.C. §119(e) of Provisional U.S. Patent Application Ser. No. 60/668,785, filed on Apr. 6, 2005, which is hereby incorporated by reference in its entirety.

TECHNICAL FIELD OF THE INVENTION

The present invention relates to systems for tracking the position of an object. In particular, the invention is a system for determining motion of the eye of a patient, using partial images from a scanning ophthalmoscope. The intended field of application of the invention is to use the tracking information to correct the position of optical treatments or optical measurements made on the patient's eye.

BACKGROUND OF THE INVENTION

Directed beams of light are used for both measurement and treatment of patients, and the patient presents a moving subject. In the field of ophthalmology, laser photocoagulation is an example of a treatment method, and optical coherence tomography an example of a measurement method, both of which are typically performed with the patient awake, and both of which require precise placement of the light beam on a portion of the eye.

A typical patient can comfortably hold his eye open for a few seconds. The eye moves considerably in one second, mainly through quick adjustments in fixation (small saccades) resulting in apparent motions of the retina on the order of one hundred microns. These motions cause noticeable errors in application of directed beams such as photocoagulation and optical coherence tomography (OCT). Tracking the motion of the eye to correct the placement of the beam has proven useful in photocoagulation [Naess, E., et al. (2002)] and in OCT [U.S. Pat. No. 6,736,508; Hammer, D. X., et al. (2005)].

Typically, a pair of rotating mirrors serves as a two-dimensional scanner to move the beam of light in two dimensions, x and y, across the subject. If motion of the subject is tracked, the positioning commands to the scanner can be adjusted so that the scan beam reaches at the desired positions on the subject.

Information on the motion of the subject must be provided with low latency so that the scanning beam is correctly positioned for each A-scan in OCT, or for each laser shot in photocoagulation. In a system that corrects the scan beam position, the latency is the time between eye motion and correction of the position of the scan beam.

Tracking methods that use two-dimensional image frames [U.S. Pat. Nos. 4,856,891; 5,729,008; 5,975,697; and U.S. Patent Application Publication No. 2005/002458] have the advantage that the two-dimensional image can also be used for a real-time display to orient the operator during the measurement or treatment procedure. These methods typically incur latency approximately equal to the time between frames, which is typically 1/30 of one second. During one frame, the eye can move significantly [Hammer, D. X., et al. (2002)]. Faster frame rates are possible, but incur extra cost.

Tracking methods that use a dithered tracking beam are fast enough to follow the motion of a human eye [Hammer, D. X. et al. (2002); U.S. Pat. Nos. 5,943,115, 5,767,941]. Dithered-beam methods with update rates of 2-10 kHz have been successful in tracking the human eye. The dithered tracking beam requires a separate optical scanning system, in addition to the system used to scan the treatment or measurement beam.

A line-scan ophthalmoscope (LSO) produces an image of the eye one line at a time [U.S. Pat. Nos. 4,732,466; 4,768,874; and 6,758,564]. In an LSO using an electronic camera, each line can be acquired and made available to digital processing within less than one millisecond. The part of the eye image contained in each line can be compared to the same area in previous eye images in order to determine the eye motion. Individual lines from an electronic LSO are available at approximately 10 kHz.

Previously disclosed tracking methods typically use a landmark, such as the optic disk. The landmark is identified first, and its location is monitored as the measurement, or treatment, scan proceeds. However, good landmarks are not always found in diseased tissue.

We see a need for a system to track motion of the eye, or other human tissue, with low latency during an optical treatment or optical measurement procedure, where the tracking system shares apparatus with a system providing a real-time display to the operator, and using a method that is independent of any particular landmark in the tissue.

SUMMARY OF THE INVENTION

The principal object of this invention is to track the position of moving human tissue, using information from a line-scan imaging system. The line-scan imaging system can provide a real-time view of the subject, in addition to tracking information.

The method of estimating motion of the subject includes the steps: (a) collect a current line of the image of the subject from the line detector in the line-scan imager, (b) compare that current line with previously-recorded lines collected from nearby areas of the subject, the comparison allowing for shifts in two dimensions, and optionally for rotation, of the current line (c) determine the shift in two dimensions, and optionally the rotation, which best aligns the current line with previously-recorded lines.

The apparatus includes: (a) a line-scan imager to collect light reflected from the subject and form an image of the subject; (b) data processing equipment to accept lines from the line-scan imager, analyze the lines to derive estimates of the current position of the subject, and output these estimates; and (c) an optical scanning system to place an optical beam on a subject, and optionally to apply the signal from the data processing equipment to correct the placement of the optical beam.

The optical beam can be either a treatment beam, such as in laser surgery, or a measuring beam, such as in optical coherence tomography. If the optical beam is a measurement beam, then a variation of this method can be used in post-processing to correct collected optical data for motion of the subject. That is, the method can be used for data registration after measurement, as well as for subject tracking during the measurement. The collected optical measurements and lines from the line-scan imager are stored with knowledge of their relative time positions, such as time stamps, so that each optical measurement can be associated with a line from the line-scan imager this line serving as the "current" line for that optical measurement. In this variation the reference frame can be built from line-scan image data taken before, during or after the scan of the measurement beam.

A specific application of this method is in an ophthalmic instrument that combines an OCT scanner and LSO, including electronics and software to cross-correlate each line acquired by the line-scan camera in the LSO with a portion of the previous frame from the LSO, so as to determine the current position of the retina relative to its position in the previous frame. This apparatus provides an estimate of the apparent position of the retina upon acquisition of each line in from the LSO. These position estimates are available with only a short delay after the eye motion occurred, so they can be used to correct the OCT scan positions so as to measure desired region of the retina in the presence of eye movements. This correction can be implemented by various methods, such as correcting the signals driving the OCT beam scanner, or by deflecting the OCT beam with correcting optics.

The embodiment described below applies this invention to a line-scan ophthalmoscope and OCT measurement system, but it will be evident to those skilled in the art that this invention can be applied to line-scan imaging of other moving subjects, and for correcting the placement of other types of optical measurement or optical treatment beams. The tracking information derived from the line-scan imager can be used to correct the line-scan image itself, for example by forming an averaged image in which the tracking information allows one to correctly place lines from several passes of the line scanner into the averaged image. The tracking information can also be used to adjust the scan range of the line-scan imager so that the region of interest remains stationary in the view of the line-scan imager.

The line-scan imager may be any imaging system that builds a full two-dimensional image in parts, and that can output partial images for digital processing before the entire image is scanned. One example is a spot-scanning confocal imager, in which the optical intensity reflected from the subject is measured one pixel at a time, with the scan typically proceeding through rows in a raster scan [U.S. Pat. Nos. 4,135,791; and 4,213,678]. A partial image, serving as the 'line' in the description of this invention, could be the set of reflected intensities in one or a few rows of the raster scan, or the set of intensities from a partial row. In this example of a spot-scanning imager, individual pixels of the partial image are recorded at different times, but if the measurements are closely spaced in time compared with the rate of changes in subject position, then the measurements are substantially simultaneous for purposes of the method disclosed here. Another example of an imaging system that builds its image in parts is an OCT scanner. An OCT scanner localizes reflections in three dimensions, and is capable of building a three-dimensional image. Each A-scan from an OCT scanner, an A-scan containing reflectivity as a function of distance along the beam, can serve as the 'line' in the method described here, with a previous two-dimensional or three-dimensional OCT image serving as the reference frame.

DETAILED DESCRIPTION

Figure 1:
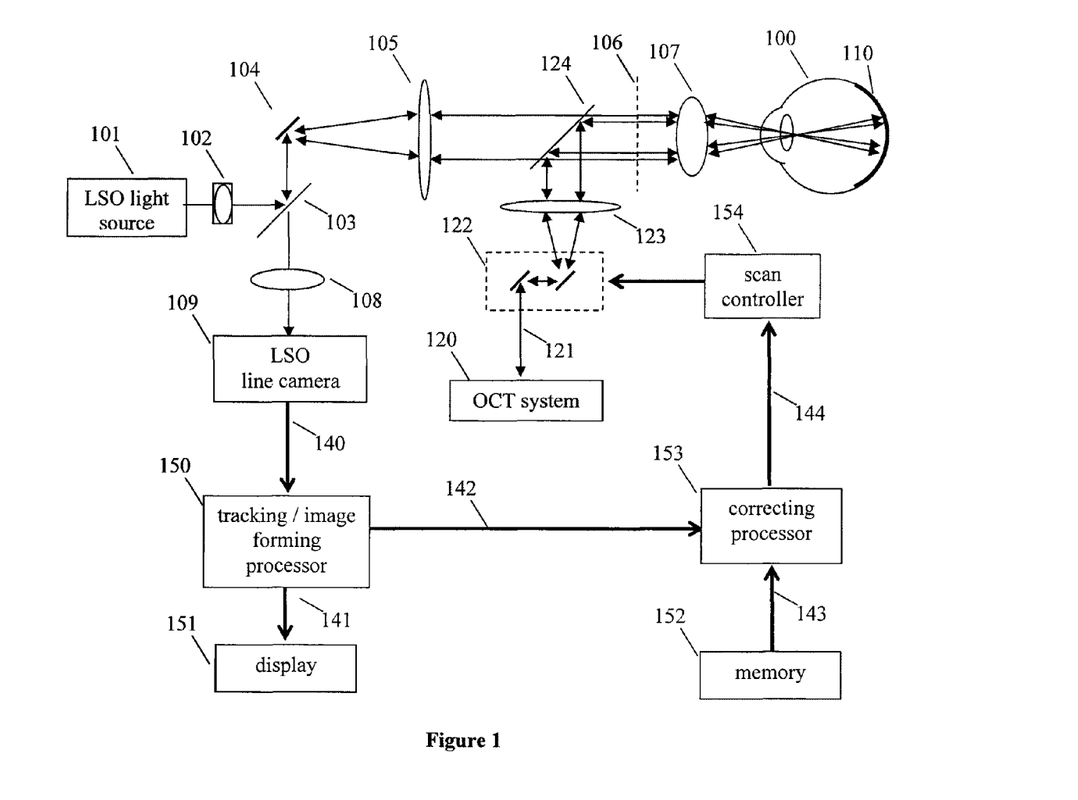
FIG. 1 illustrates a combination imaging and optical measurement system applied to the human eye.

FIG. 1 is a schematic illustration of an OCT measurement system incorporating eye tracking based on a line-scan ophthalmoscope (LSO). Light from the LSO light source 101 is routed by cylindrical lens 102 and beamsplitter 103 to scanning mirror 104. The cylindrical lens 102 and the scan lens 105 produce a line of illumination at the retinal image plane 106, and the ocular lens 107 and optics of the human eye 100 re-image this line of illumination onto the retina 110. The line of illumination is swept across the retina as the scanning mirror 104 rotates. Reflected light from the retina approximately reverses the path of the LSO illumination light; the reflected light is de-scanned by the LSO scan mirror 104 so that the illuminated portion of the retina is continuously imaged by imaging lens 108 onto the LSO line camera 109. The LSO line camera converts the reflected LSO light into a data stream 140 representing single-line partial images, which are processed to form both eye tracking in formation and a real-time display of the retina.

The OCT system 120 incorporates the light source, light detector or detectors, and processor required to determine the depth profile of backscattered light from the OCT beam 121. One type of OCT system is described in the reference by Huang et al. OCT scanner 122 sweeps the angle of the OCT beam in two dimensions, under the control of scan controller 154. Scan lens 123 brings the OCT beam into focus on the retinal image 106. Beamsplitter 124 combines the OCT and LSO beam paths so that both paths can more easily be directed through the pupil of the human eye 100. (Combining the beam paths is not required in direct imaging applications, where the object itself lies in the location of retinal image 106.) If the OCT and LSO use different wavelengths of light, beamsplitter 124 can be implemented as a dichroic mirror. The OCT beam is re-focused onto the retina through ocular lens 107 and the optics of the human eye 100. Some light scattered from the retina follows the reverse path of the OCT beam and returns to the OCT system 120, which determines the amount of scattered light as a function of depth along the OCT beam.

As noted above, the eye 100 may move with respect to the measurement system causing the correspondence between the position of scanner 122 and positions on retina 110. In some optical measurement or optical treatment systems, such as those using handheld scanners, motion of the scanning optics can contribute to the relative motion between scanner coordinates and sample coordinates.

The stream of partial images 140 from the LSO camera are provided to a processing routine described below and represented by block 150 in FIG. 1. One output of the processing routine is a series of complete frames 141 providing the operator with a real-time view of the subject, via display 151. Another output of the processing routine is series 142 of estimates of the current displacements of the eye. These estimates of current displacement can be combined with the set 143 of locations on the subject at which OCT measurements are desired, to form a set of corrected scan coordinates 144 provided to the scan controller 154 so that the scanner 122 directs the OCT beam to the desired location on the eye.

An LSO operating at 20 frames per second, with 512 lines per frame, provides 10,000 lines per second. We use a digital line-scan camera, so with appropriate hardware each of these lines is available for processing within 100 microseconds after the instant the light was reflected from the eye.

Figure 2:
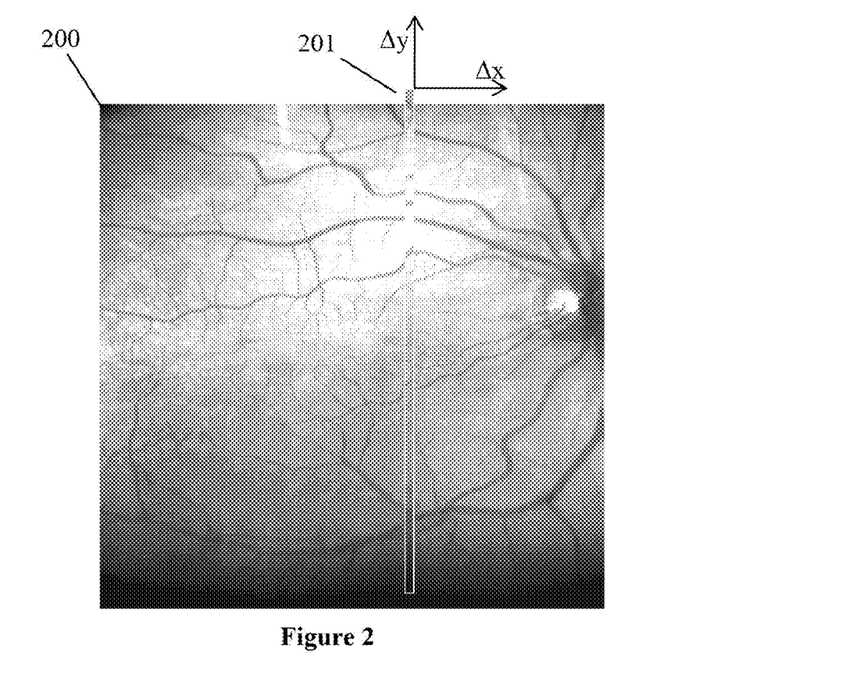
FIG. 2 shows a fundus image from a human eye, and a representation of a partial fundus image from a line-scan ophthalmoscope

Each line from the LSO is compared with a reference frame, at a range of shifts in x and y. FIG. 2 shows a two-dimensional image 200 of a human retina built from an LSO.

A single line from the LSO produces a vertical line such as 201. (Line 201 is represented in FIG. 2 by a strip of several lines for better visibility.) In the method of this invention line 201 is conceptually shifted across reference frame 200 until a good match is found. If the eye has not moved, one can predict that line 201 will match that portion of reference frame 200 that has the same scanner coordinates as line 201, the same position of the LSO scanner and the same shift along the line-scan camera. If the eye has moved, relative to the coordinate system of the scanner, line 201 and the matching portion of reference frame 200 will have different scanner coordinates.

Figure 3:
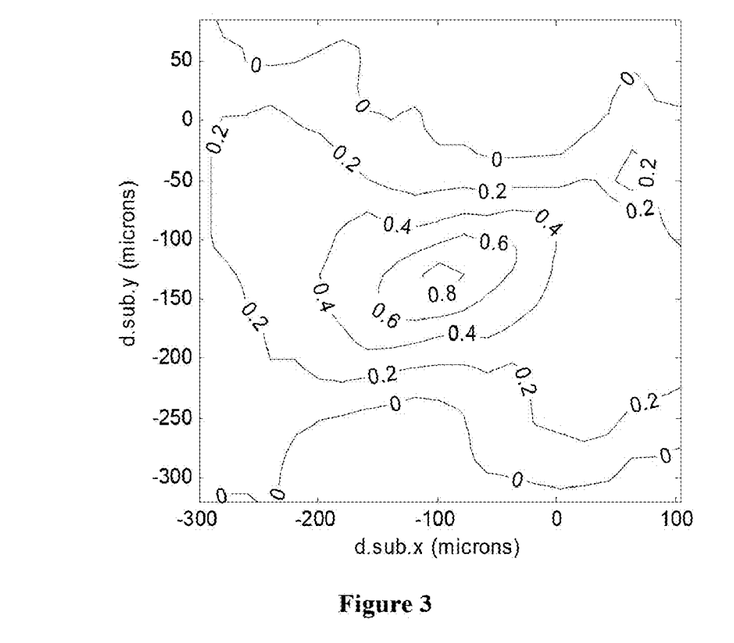
FIG. 3 shows the cross-correlation function between the partial image and the full image.
Figure 4A:
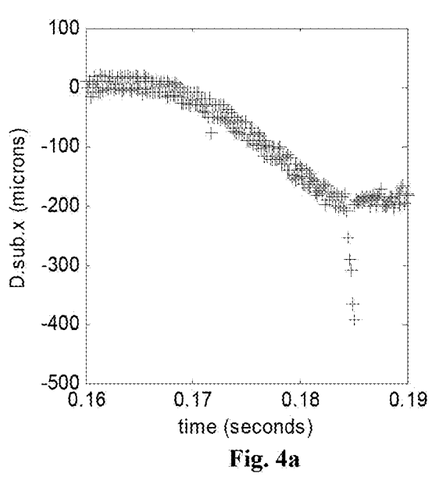
FIG. 4 plots estimates of eye position as a function of time.
Figure 4B:
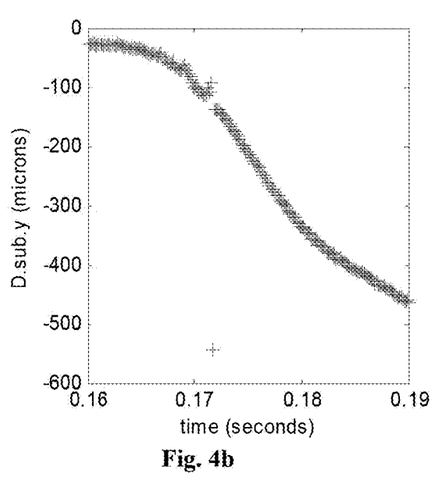
Figure 4C:
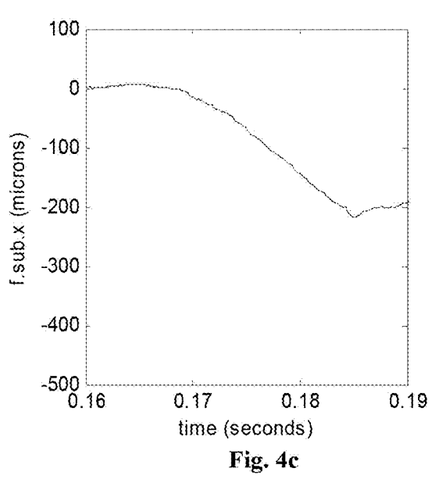
Figure 4D:
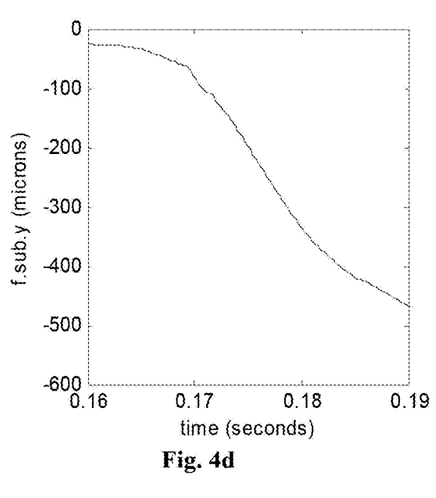

The comparison between the line 201 from the LSO and the reference frame 200 can be done using a cross-correlation, forming a cross-correlation function C(d) where the vector d=($\Delta$x, $\Delta$y) represents the shift. The cross-correlation function is computed from the image intensities in the current line L(r) and in a group of previously-acquired lines forming a two-dimensional reference frame A(r), in which the vector r=(x,y) denotes position on the retina. It is advantageous to use the normalized cross-correlation, which takes the value of 1 when the two sub-images L(r) and A(r) match exactly, $$C(d) = \sum_r A(r-d) \cdot L(r) \bigg/ \sqrt{\sum_r A^2(r) \cdot \sum_r L^2(r)},$$

in which the sum is taken over the locations r in the current line. An example of a cross correlation function between a line and reference frame acquired from the retina of a human eye are plotted in FIG. 3. FIG. 3 is a contour plot of value of C(d) as a function of the components $\Delta$x, $\Delta$y of the shift d. The normalized cross-correlation reaches a peak of 0.8 at a shift of $\Delta$x=−100 μm, $\Delta$y=−130 μm, compared with lower values at other shifts. This match indicates that the retina has moved 100 μm to the left and 130 μm down between acquisition of the reference frame and acquisition of the current line from the LSO.

Efficient methods of computing cross-correlations, including computation using the fast Fourier transform, are well known in the art and these efficient methods are preferably used with this invention. Another advantageous technique is to compute the cross-correlation of intensities after spatially high-pass filtering, so as to retain detail associated with the tissue but attenuate large-scale variation such as non-uniform illumination. In addition, low-pass filtering the intensities can be useful for reducing noise in the computed cross-correlation function.

The cross-correlation will often have a peak as a function of d, the location of that peak indicating the shift d that best aligns the current line with the reference frame. This peak location is one choice for our estimate D of subject motion since acquisition of the reference frame. An alternative estimate is the centroid of the cross-correlation function, D=$\Sigma$dC(d)/$\Sigma$C(d) where the sum is taken over all considered shifts d. Such calculations can be weighted by our a-priori expectation G(d) that the subject has shifted by d since acquisition of the reference frame: D=$\Sigma$dG(d)C(d)/$\Sigma$G(d)C(d).

The shift d represents the subject motion between acquisition of the line L(r) and acquisition of the reference frame A(r). An important aspect of this invention, however, is that the cross-correlations can be evaluated upon acquisition of each line. Therefore the time between estimates D is only the time between acquisition of successive lines. Successive values of D are expected to differ by only the small motion possible in the short time between acquisition of successive lines. The correction signal provided by this tracker (for application either to correct an optical scan or to register a previously-acquired data set) can be a series of very small corrections, corresponding to the motion of the subject between successive line acquisitions.

Previous tracking information can be used in the a-priori expectation G(d). For example G(d) may be a function peaked at the expected shift, based on recent motion of the subject, with a width consistent with recent uncertainty in the system and physically reasonable velocity and acceleration of the subject. It is not necessary to compute the cross-correlation at shifts d outside the range of a-priori expectations, allowing savings of computational time.

Alternative to the cross-correlation C(d), other measures of similarity between the sub-images can be used. Two commonly-used measures are the sum of squared differences and sum of absolute differences, these quantities being minimized for well-matched sub-images.

Human eyes rotate slightly about the optical axis. The shift d can optionally be generalized to include rotations by rotating the previous frame, interpolating data points where necessary, before the cross-correlation. In this case the offset of the vector r indicated above by the vector subtraction (r−d) must be generalized to include rotation of r.

Alternatively to rotating the previous frame, cross-correlation under a rotation angle can be estimated by cross-correlating separate portions of the current line with the previous frame, considering only shifts d without rotation, to derive individual cross-correlation functions $C_i$(d). The overall cross correlation function can be evaluated at any rotation θ by forming the sum C(d)=$\Sigma C_i$(d+θ$e_i$) where the vectors θ$e_i$ are the displacements of the centers of each portion of the current line caused by rotation through and angle θ. (Considering the added shifts θ$e_i$ only at the centers of the portions of the current line is an approximation, because the image details that most influence the cross-correlations may not be centered in these portions of the current line.)

The range of shifts d can optionally be limited, given knowledge of the characteristics of subject motion, specifically of human eye fixation. For example, it is practical to scan the retina of the human eye at 30 frames per second, with 512 lines in each frame (requiring a 15 kHz line rate from the LSO camera). Given a relatively fast shift in gaze, 300°/sec, the eye could rotate 10° between frames, shifting the apparent position of the retina by approximately 3 mm. Between successive lines, however, the apparent position of the retina would move only 6 μm since the last position estimate. Given the possibility of short segments of bad position estimates, as discussed below, it is practical to search a range of shifts d spanning 100 μm horizontally and vertically. Rotation of the image of the retina can be caused by so-called torsional rotation of the eye. The torsion angles are a fraction of the rotation angles of the eye, and between successive lines the rotation of the retinal image will be less than 2 millidegrees. If one chooses to correct for this rotation, it is sufficient to search a 50-millidegree range of angles θ.

Additionally, one can cross-correlate each line with local lines within the same frame. Cross-correlation of neighboring lines gives mainly information on motion along the length of these lines. Acceleration perpendicular to the length of the line is revealed in the relative correlation between a given line and its immediate neighbors to each side.

Pattern noise in typical line-scan cameras tends to bias the cross-correlation toward certain shifts. To reduce this bias one can optionally correct for pattern noise using standard techniques including look-up tables.

There is uncertainty in the estimate of motion. When the LSO scans relatively featureless sections of the eye, the image data returned often lacks detail, and there is no shift where the match to the reference frame is clearly superior; that is there is sometimes no peak in C(d). One can estimate the uncertainty from the shape of the peak in the cross-correlation function C(d). By way of example, the cross-correlation value C(d), optionally multiplied by the a-priori likelihood G(d), can be used as a measure of the likelihood that the actual eye shift was d. The eye shift could be estimated by D=ΣdG(d)C(d)/ΣG(d)C(d), assuming that the data has been preprocessed such that C(d) approaches zero for un-related images. An example method of preprocessing is to high-pass filter the images before convolution then optionally to set to zero values of C(d) below a certain threshold. The corresponding uncertainty is $[\Sigma(d-D)^2 G(d)C(d)/\Sigma G(d)C(d)]^{\wedge}(0.5)$.

As an additional example, the magnitude of the peak in C(d) is a measure of the confidence in the estimate D; the inverse of this magnitude can serve as an uncertainty in D. As a further example, the area in d over which C(d) exceeds a chosen threshold indicates the range of likely shifts D; the square-root of this area can serve as an uncertainty in D.

The position information and uncertainty estimates can be monitored to indicate to the operator the current quality of the tracking data, and the current state of the subject. In an ophthalmic device, the amount of eye wander can be quantitatively indicated to the operator, indicating when the patient may be beginning to tire.

The position estimates D are obtained upon acquisition of each line from the line-scan imager. These line acquisitions may come more quickly than the subject moves. Groups of position estimates D can be averaged, preferably weighted according to their uncertainties, and further optionally weighted according to their age, to form estimates with reduced noise. (Alternatively, estimates D with particularly large uncertainty can be simply discounted for purposes of tracking.)

This tracking method makes use of a reference frame. Any given frame captured by a line-scan imager can be distorted by motion occurring during acquisition of that frame, so the possible distortions within the reference frame must be considered. One approach is to build a reference frame from an initial set of N acquired frames. Within the data set comprising the first N frames, lines from frame 2 onward are compared to the first frames to form a stream of estimates of displacement D(t) in the manner described above. This stream of estimates suffers from errors if there was eye motion during the first frame, but such motion can be discovered by analysis of D(t). For example, the first time derivative of D(t) yields a velocity V(t) that will have peaks corresponding to each saccade of the eye. The problem of motion during the initial frame manifests itself as peaks in V(t) that repeat every time the LSO scanner re-traces a particular portion of the eye. If one plots the estimated velocity V(t) as a function of position on the eye, then the resulting N−1 plots will show common features due to motion during the first frame. The median over these N−1 plots is a good estimate of the negative of the eye velocity during that first frame. From the velocity estimate given by this median, on can integrate to form position estimates for the first frame, and correct the data stream D(t) for the effects of motion during the first frame. Now having position-corrected image data from all N frames, one can combine the N frames of image data to form a reference frame free from motion artifacts. Other methods of building motion-artifact-free images are known in the field of medical imaging (for example, U.S. Pat. No. 5,575,286). The construction of a reference frame from data acquired on a moving eye will move image data around, so that portions of the reference frame are associated with scanner coordinates different from the scanner coordinates at which those portions were originally acquired.

There are periods of unreliable data, both serious (blinks) and mild (scanning a relatively featureless region). There may also be periods without data. For example, in a line-scan ophthalmoscope scanning repeatedly in one direction, the period required for the scanner to return to the starting position is a period of time during which no position information is available. It is advantageous to minimize the duration of these periods. For example, in a line-scan imager it is advantageous to operate with bi-directional scanning.

One can provide a continuous stream of position estimates through periods of unreliable or missing data, by using the uncertainty estimates described above to weight the contributions of individual estimated shifts D(t) in determining the estimated eye position X(t). As an example, one particular method of combining the stream of estimated shifts D(t) is to perform a weighted fit to a function $f(t)$. The fitting function could be for example a linear or quadratic polynomial. After each line scan, the value of the fitting function at the end of the data stream provides an improved estimate of the shift. During periods of unreliable data, earlier data will more strongly influence the fit, and the values of the fitting function effectively extrapolate from these earlier measurements. When the estimated shifts become reliable again, these low-uncertainty estimates strongly influence the fit, and the values of the fitting function return to follow the stream D(t). It is useful to have the uncertainties in the stream of estimated shifts D(t) grow as the age of the data increases, so that old estimates smoothly lose their influence in the fit.

Knowledge of possible motion of the subject, such as physical limits on accelerations and velocities, allows more robust fitting by reducing the weight of estimated shifts that are inconsistent with possible motion of the subject.

FIG. 4 shows plots of the measured and fit positions of a human eye retina based on the data stream from an LSO. (More specifically, we plot of the apparent position of the retina, as seen through the human eye optics.) Each of the points marked with '+' signs in FIGS. 4*a* and 4*b* are estimates $D(t_n)$ of the eye motion, where the integer n counts the successive lines returned by the LSO. FIG. 4*a* shows horizontal (x) components of motion and FIG. 4*b* shows vertical (y) components. (A few of these estimates lie above or below the range of the plots.) For this data, the fitting functions $f_n(t)$ were straight-line segments fit to the most recent fifty estimates $D(t_n)$. We used a weighted fit, with the weights assigned to each estimate $D(t_n)$ based on the value of the cross-correlation $C(D(t_n))$, based on the age of the data point, and also based on our estimate of the a-priori likelihood of the eye being in this position. The a-priori likelihood is determined from how close the current estimate of position comes to extrapolation of the previous fit. Specifically, the relative weight assigned to each estimate $D(t_n)$ was $C(D(t_n))^* \exp[t_n/\tau]^* \exp[|D(t_n)-f_{n-1}(t_n)|/a]$ where the best parameters a≈15 μm and τ≈2.5 msec were found through experimentation. With each new estimate D a new fit is performed. The solid curves in FIGS. 4*c* and 4*d* are plots of the resulting sequence $f_n(t_n)$: the values of the updated fitting functions $f_n$, each evaluated at the times $t_n$ corresponding to the latest line returned from the LSO.

The scan range of a line-scan imager is generally easily adjustable. It may be advantageous in the implementation of this method to narrow the scan range to cover regions of the subject containing detail useful for tracking. The narrow range can be scanned during periods when tracking information is critical, and widened at other times. The narrow range can be shifted to remain on the regions of the subject with relatively more detail, using the data from the tracking system itself. Using the tracking data to adjust the scan forms a control loop. The low latency of this line-based tracking method is advantageous in the implementation of such a control loop, as is well known in the art of feedback control.

This tracking method allows adaptations to save computational time.

(1) A shift estimate can be computed for only one or more selected lines in each newly-acquired frame. That is, if a line L(r) is expected to produce a noisy maps C(d) one may want to skip computation of C(d). One can process just those lines containing relatively detailed structure, these lines giving the most accurate position estimates. In this way one spends his computational resources on those lines that yield the most information. The amount of detail can be estimated with a small fraction of the effort required to compute C(d), for example by computing the autocorrelation of a single line. The locations of useful detail in the object remain the same from scan to scan, so an estimate of the value of each line is available from previous lines covering the same area.

(2) The cross-correlations may be done by fast Fourier transform (FT) along the direction of the line-scan camera. The forward FT of previous lines can be saved. For each line, one can perform the forward FT, and pointwise multiply with saved FTs within the range of plausible shifts to compute the FT of the cross-correlation functions. The root-mean-square (RMS) of these pointwise products gives the RMS of C(d) along the corresponding line. The reverse FT is performed only for a few products with the largest RMS.

(3) The operation count for the fast FT can be significantly reduced using a-priori knowledge if the range of shifts d over which the peak in the cross-correlation function C(d) may be found. This means that shorter arrays can be used in numerical computation of C(d). The preferred implementation smoothes and then sub-samples the stored FTs of lines from the line-scan camera; these sub-sampled arrays have typically ⅛ the number of elements as the full array. The operations that are repeated several times per line from the line-scan camera, the pointwise multiply and reverse FT, are thus performed on significantly shorter arrays, providing a significant improvement in computational speed.

We estimate the computational resources required. The cross correlation need only be computed over a limited range of shifts d. Taking for example the case of shifts only, without rotation, we estimate the largest believable eye shift between lines, in units of pixels. Dead time between sweeps should be avoided; bi-directional LSO sweeping is preferred. The distorted information at the ends of the sweep, due to the gradual change in direction of the scanner, can be used with the tracking system, taking care to account for the different delta-x between lines. By way of example we consider a bi-directional triangle-wave scan with 500 acquisitions of the line-scan camera covering 10 mm of tissue. If there is 1 millisecond during which the scanner covers tissue not included in the reference frame, then eye rotation of 350 degrees per second (100 mm/sec apparent motion of the retina) could move retinal tissue by 0.1 mm, which corresponds to 5 acquired lines.

We can now estimate the number of multiplications required to build the cross-correlation map C(d) for each line acquired by the LSO. One can use FT-based correlation calculations in 1 dimension along the full-length of each line. Each line in the reference frame has already had a FT calculated; if these previous results are stored, we need only do the FT on the current line. One then multiplies the current line by each stored line from the reference frame within the range over which eye motion is possible, and performs an inverse FT on the product with the largest rms value. If one searches over 5 lines from the reference frame, then the number of multiplications required for the steps listed in this paragraph is approximately $2N \log_2 N + N*2*5 + 2N \log_2 N$, where N denotes the number of pixels in a line. For 512 pixels in a line, this is 25,000 multiplies. If one uses a TMS320-family DSP running at 1 GHz to execute 3600 Mmac/sec, building C(d) for each line from the LSO requires only 7 microseconds.

Fitting the data stream D(t) can be done with a small operation count. Linear least-squares fitting uses sums of the form $\Sigma(f(t_i)D_i/\tau_i^2)$ where f(t) is one of the components in the fitting function, $D_i$ is a component of the estimated eye position, and $\tau_i$ is the uncertainty. If there are P free parameters in the fitting function, the fit parameters come from solution of a matrix equation involving a P×P matrix containing such sums; solution of this matrix equation requires only $P^3$ multiplies. These sums themselves can be updated with $P^2$ additions for each line scanned. P is likely to be small, 2 or 3, so this operation count is insignificant compared with the operation count for the cross-correlations.

We have disclosed a method of using sections of an image, in the order in which they are acquired, to derive multiple measurements of the motion of the subject in the time required to build a full image. Some imaging systems that can be used with this method are: a flying-spot confocal microscope, a line-scan imager, and an OCT scanner. One potential subject of the method is the human eye. Some uses of the measurements of subject motion are to correct the positions of an optical beam, and to correct the interpretation of an optically-acquired data collected concurrently with the position measurements. The image acquired can also serve as a real-time display for the operator.

The optical beam being corrected can be a diagnostic beam, such as the probe beam in an OCT system. The determination of the motion is made by comparing a current sub-image with a previous sub-image. The current sub-image can be a single line from the line-scan imager, or a number of lines from the line-scan imager. The comparison can be made by cross-correlation of intensities in the two sub-images to be compared, or by computing the sum of absolute differences between the intensities in the two sub-images to be compared, or by other means of comparison to discover the shift of the subject between acquisition of the two sub-images. The estimate of the shift can be the centroid of the cross-correlation function, or the peak of the cross-correlation function, or another means to estimate the shift based on comparison of the two sub-images. The uncertainty in these estimates can be determined using the second moment of the cross-correlation function, or from the area within the cross-correlation function under a certain threshold, or other means. The uncertainties can be used to derive, from a series of shift estimates, a best current estimate of the subject position, for example by least-squares fitting the shift estimates to a function of time. A-priori information about the possible motion of the subject can be used to decrease the weight in the fit given to outliers in the series of shift estimates. The range of shifts that are compared is limited based on current knowledge of the subject position. The sub-images to be used in the computations of correlation can be selected based on the amount of useful-detail in these sub-images; one method of estimating the useful detail is to compute the autocorrelation function and to estimate the uncertainty in a shift as we would for a cross-correlation function. The scan range of the imaging system can be limited to cover regions of the subject with useful detail. The scan range can be selected to cover the area of the subject containing the most useful detail.

One apparatus in which this method can be applied is an ophthalmic system comprising an OCT scanner and an LSO. The LSO can provide a real-time view of the subject being scanned by OCT. The apparatus can additionally provide electronics such as a digital signal processor (DSP) or microprocessor, and software, or other means to derive position estimates from each line from the LSO. Alternatively to using software and a processor, the derivation of position estimates can be implemented in programmable logic devices. The apparatus can include a second set of scan mirrors, additional electronic inputs to the beam scanner, or other means to correct the OCT scan position based on these position estimates.

Although various embodiments that incorporate the teachings of the present invention have been shown and described in detail herein, those skilled in the art can readily devise many other varied embodiments that still incorporate these teachings.

The following references are hereby incorporated herein by reference.

U.S. Patent Documents

U.S. Pat. No. 4,135,791
U.S. Pat. No. 4,213,678
U.S. Pat. No. 4,732,466
U.S. Pat. No. 4,768,873
U.S. Pat. No. 4,856,891
U.S. Pat. No. 5,575,286
U.S. Pat. No. 5,644,642
U.S. Pat. No. 5,729,008
U.S. Pat. No. 5,767,941
U.S. Pat. No. 5,943,115
U.S. Pat. No. 5,975,697
U.S. Pat. No. 6,283,954
U.S. Pat. No. 6,325,512
U.S. Pat. No. 6,758,564
U.S. Pat. No. 6,726,325
U.S. Pat. No. 6,736,508
U.S. Pat. No. 6,769,769
U.S. Published Application 20050024586
U.S. Published Application 20050140984
U.S. Published Application 20030199769
Co-pending U.S. application Ser. No. 11/331,567, filed Jan. 13, 2006, entitled "Method of Motion Correction in Optical Coherent Tomography Imaging"

Other Publications

Huang, D. et al. *Science* 254 (5035): 1178-81 (1991).
Hammer, D. X. et al. "Image Stabilization for Scanning Laser Ophthalmoscopy" *Optics Express* 10 1549 (2002)
Naess, E. et al. "Computer-assisted laser photocoagulation of the retina—a hybrid tracking approach" *Journal of Biomedical Optics* 7 (2): 179-189 (2002).
Hammer, D. X. et al. "Active retinal tracker for clinical optical coherence tomography systems" *Journal of Biomedical Optics* 10 (2): 0240380-1 (2005).
Rogers, J. A., et al. "Topography and volume measurements of the optic nerve using en-face optical coherence tomography." *Optics Express* 9 (10): 533-545 (2001).

What is claimed is:

1. An apparatus for measuring the eye comprising:
an optical coherence tomography (OCT) system having a radiation beam which is scanned over the eye;
a line-scan ophthalmoscope (LSO) for generating an image of the retina by scanning a line of light across the retina and collecting the reflected light; and
a processor for controlling the OCT and LSO, said processor for capturing image data from the LSO corresponding to a position of the line of light on the retina and comparing the image data to a reference image to determine if the eye has moved and using that information to correct the positioning of the radiation beam used by the OCT.

2. An apparatus as recited in claim 1, wherein the image generated by the LSO is displayed in real time to the user.

3. An apparatus as recited in claim 1, wherein the processor determines if the eye has moved by comparing the image data with the reference image to find a substantially matching image portion and determining a displacement between scan coordinates associated with the matched image portions, said displacement corresponding to the motion of the eye.

4. An apparatus as recited in claim 1, wherein the processor compares the captured image data and selected portions of the reference image using a cross correlation technique.

5. An apparatus as recited in claim 4, wherein portions of the reference image which are selected for the comparison by the processor are chosen based in part on previous estimates of eye motion.

6. An apparatus as recited in claim 1, wherein the processor compares various portions of the image data to the reference image and uses a combination of the results to correct the positioning of the radiation beam used by the OCT.

7. An apparatus as recited in claim 6, wherein the processor analyzes the combination of the results using a curve fitting algorithm.

8. An apparatus in claim 1, wherein the processor controls the scanning of the LSO to image selected regions of the eye that have more detail than other regions.

9. An apparatus for measuring the eye comprising:
an optical coherence tomography (OCT) system having a radiation beam which is scanned over the eye;
a confocal optical imager for generating an image of the retina independent of the OCT system, said image being generated by scanning an illumination spot on the retina and collecting the reflected light; and
a processor for controlling the OCT and the scanning optical imager, said processor for capturing image data from the imager and comparing the image data to a reference image to determine if the eye has moved and using that information to correct the positioning of the radiation beam used by the OCT.

10. An apparatus as recited in claim 9, wherein the image generated by the confocal imager is displayed in real time to the user.

11. An apparatus as recited in claim 9, wherein the processor determines if the eye has moved by comparing the image data with the reference image to find a substantially matching image portion and determining a displacement between scan coordinates associated with the matched image portions, said displacement corresponding to the motion of the eye.

12. An apparatus as recited in claim 9, wherein the processor compares the captured image data and selected portions of the reference image using a cross correlation technique.

13. An apparatus as recited in claim 12, wherein portions of the reference image which are selected for the comparison by the processor are chosen based in part on previous estimates of eye motion.

14. An apparatus as recited in claim 9, wherein the processor compares various portions of the image data to the reference image and uses a combination of the results to correct the positioning of the radiation beam used by the OCT.

15. An apparatus as recited in claim 14, wherein the processor analyzes the combination of the results using a curve fitting algorithm.

16. An apparatus in claim 9, wherein the processor controls the confocal microscope to image selected regions of the eye that have more detail than other regions.

* * * * *

UNITED STATES PATENT AND TRADEMARK OFFICE
CERTIFICATE OF CORRECTION

PATENT NO.       : 8,050,504 B2
APPLICATION NO.  : 12/861672
DATED            : November 1, 2011
INVENTOR(S)      : Matthew J. Everett et al.

It is certified that error appears in the above-identified patent and that said Letters Patent is hereby corrected as shown below:

On cover page, item (73), in "Assignee", in column 1, line 1, delete "Carl Zeis Meditec, Inc.," and insert -- Carl Zeiss Meditec, Inc., --, therefor.

On page 2, under "OTHER PUBLICATIONS", in column 1, line 4, delete "trackerr" and insert -- tracker --, therefor.

On page 2, under "OTHER PUBLICATIONS", in column 1, line 4, delete "clinocal" and insert -- clinical --, therefor.

On page 2, under "OTHER PUBLICATIONS", in column 1, line 5, delete "cohernce" and insert -- coherence --, therefor.

On page 2, under "OTHER PUBLICATIONS", in column 2, line 13, delete "measuremetns" and insert -- measurements --, therefor.

On page 2, under "OTHER PUBLICATIONS", in column 2, line 16, delete "minature" and insert -- miniature --, therefor.

In column 3, line 64, after "ophthalmoscope" insert -- . --.

In column 6, line 57, delete "50-millidegree" and insert -- 50 millidegree --, therefor.

In column 10, line 14, delete " $\Sigma(f(t_i)D_i/\tau_i^2)$ " and insert -- $\Sigma(f(t_i)D_i/\sigma_i^2)$ --, therefor.

Signed and Sealed this
Twenty-seventh Day of March, 2012

David J. Kappos
*Director of the United States Patent and Trademark Office*

In column 10, line 16, delete "$\tau_i$" and insert -- $\sigma_i$ --, therefor.

In column 11, line 51, after "Imaging"" insert -- . --.

In column 11, line 57, after "(2002)"" insert -- . --.

In column 12, line 39, in claim 8, delete "apparatus in claim 1," and insert -- apparatus as recited in claim 1, --, therefor.

In column 14, line 4, in claim 16, delete "apparatus in claim 9," and insert -- apparatus as recited in claim 9, --, therefor.